United States Patent
Baiardo et al.

(10) Patent No.: US 6,469,525 B2
(45) Date of Patent: Oct. 22, 2002

(54) METHOD FOR SENSING HUMIDITY IN A TAPE LIBRARY

(75) Inventors: Jonathan C. Baiardo, Fort Collins, CO (US); Kelly John Reasoner, Ft. Collins, CO (US); Duane L. Harmon, Loveland, CO (US); Richard A Irwin, Fort Collins, CO (US)

(73) Assignee: Hewlett-Packard Company, Palo Alto, CA (US)

( * ) Notice: Subject to any disclaimer, the term of this patent is extended or adjusted under 35 U.S.C. 154(b) by 0 days.

(21) Appl. No.: 09/754,984

(22) Filed: Jan. 4, 2001

(65) Prior Publication Data

US 2002/0084789 A1 Jul. 4, 2002

(51) Int. Cl.⁷ .............................................. G01R 27/26
(52) U.S. Cl. ..................... 324/689; 324/667; 73/335.04
(58) Field of Search ....................... 340/602; 73/335.02, 73/335.04; 324/689, 665, 667, 664; 711/111; 702/132

(56) References Cited

U.S. PATENT DOCUMENTS

| | | | | | |
|---|---|---|---|---|---|
| 4,282,480 A | * | 8/1981 | Fujito | .......................... | 324/665 |
| 4,662,220 A | * | 5/1987 | Laue | ........................... | 324/667 |
| 5,230,055 A | * | 7/1993 | Katz | ........................... | 702/132 |
| 5,287,478 A | * | 2/1994 | Johnston | ..................... | 711/111 |

\* cited by examiner

*Primary Examiner*—Christine K. Oda
(74) *Attorney, Agent, or Firm*—John R. Pessetto

(57) ABSTRACT

An electrical system for measuring humidity which is capable of measurements accurate to +/−6 percent from board to board. The accuracy provided by this electrical system makes it possible to correlate errors in data on backup magnetic tapes to variations in humidity. The electrical system consists of an oscillator whose frequency is dependent on the capacitance of a capacitor used in the circuit. The capacitance value of the capacitor is dependent on the relative humidity. The frequency of the oscillator is translated to a humidity value by an electronic counter and a microprocessor.

2 Claims, 1 Drawing Sheet

METHOD FOR SENSING HUMIDITY IN A TAPE LIBRARY

FIELD OF THE INVENTION

This invention relates generally to humidity sensing and more specifically to sensing humidity in a computer tape backup library.

BACKGROUND OF THE INVENTION

Since the advent of programmable information processing systems, the need to store information has grown dramatically. Information storage is frequently accomplished through devices, which interconnect with a computer and act relatively independently of it in response to signals received from the main data processing functions of the computer. These devices, known as peripheral devices, act to receive data from the main computer memory and then to store such data on a separate media within the peripheral device. One of the aspects of typical memory devices and computer systems is their volatility. They may unintentionally lose their contents occasionally. This may be due to hard disk failures, computer virus attacks, or other reasons. To overcome these limitations, backup devices have evolved. Such devices serve the simple function of separately storing large amounts of data on relatively non-volatile media. In the field of these specialized devices, the use of magnetic tape media has become one of the most used. After data is stored on magnetic tapes, the tapes may be stored in a controlled environment that reduces the probability of the data on the tapes being corrupted. One of the parameters that may be controlled in order to reduce tape failures is humidity.

Humidity may affect, how well or if at all, a magnetic tape functions. Tape failures due to humidity may cause downtime and loss of data. It is important therefore, to track the occurrence of downtime and data loss as a function of relative humidity (%RH). When a correlation between the occurrence of downtime and data loss versus %RH is established, a %RH value may be chosen which results in the lowest occurrence of downtime and data loss. In addition, %RH measurements may be used to indicate when the %RH in the area where the tapes are stored is deviating from an ideal value. In this way, tape failures may be reduced by correcting the %RH to a proper level before failures occur. In order to most effectively track failures based on %RH, measurement of %RH should be as accurate as possible.

SUMMARY OF THE INVENTION

The invention measures the relative humidity of an environment and stores the data for later reference or immediate display. The invention uses a capacitor whose capacitance is a function of the relative humidity sensed by the capacitor. This capacitor is used in conjunction with a comparator to output a series of pulses. The frequency of these pulses is dependent on the capacitance of the capacitor and is counted by a counter that sends data to a microprocessor where the count is mapped to a relative humidity value. This value can then be stored for reference or displayed immediately.

Other aspects and advantages of the present invention will become apparent from the following detailed description, taken in conjunction with the accompanying drawing, illustrating by way of example the principles of the invention.

DETAILED DESCRIPTION OF THE PREFERRED EMBODIMENT

Figure 1:
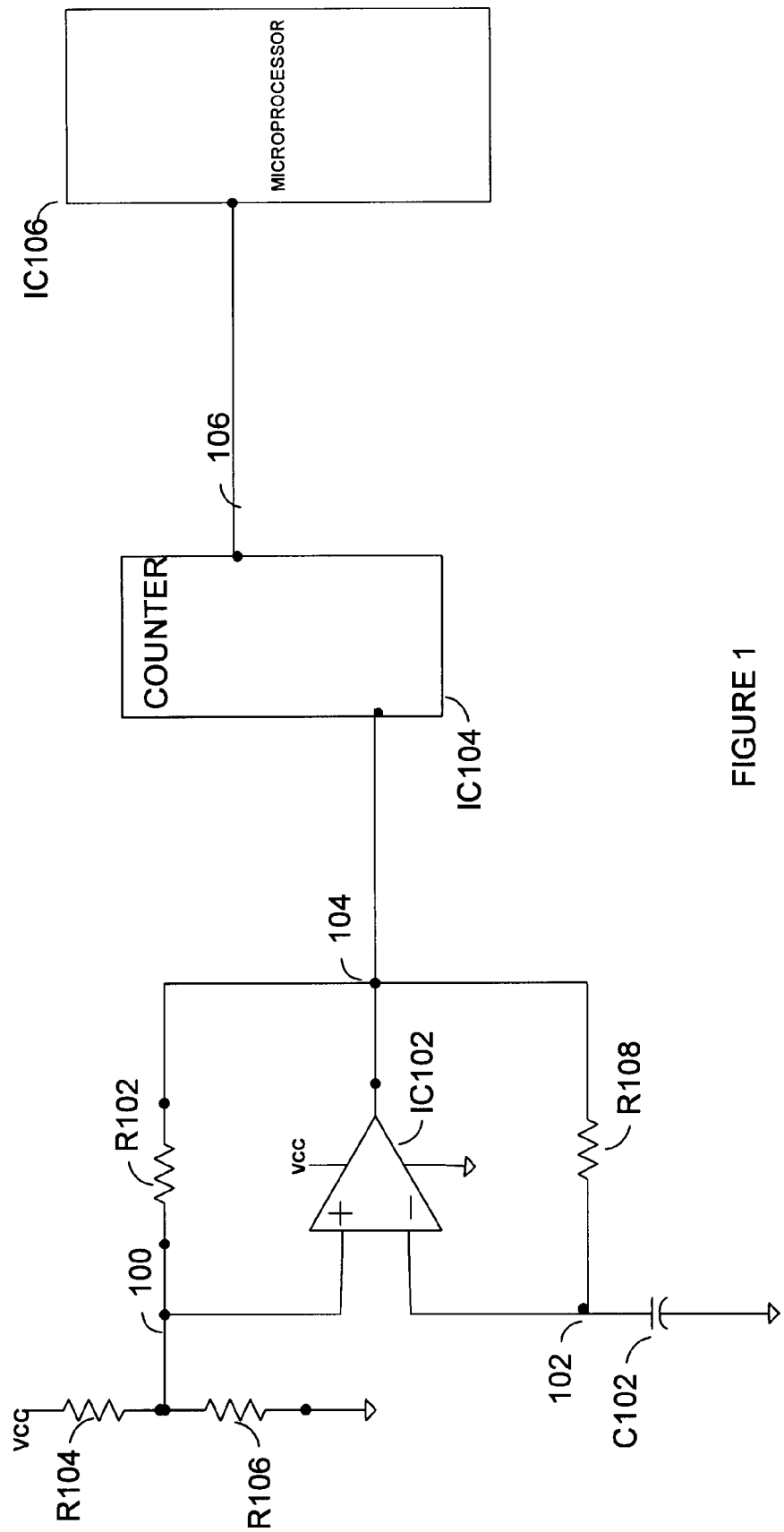
FIG. 1 is a drawing showing the elements used to measure and store measured relative humidity values.

This humidity sensor is based on a capacitor whose value varies based on the humidity where the capacitor is stored. The manufacturers of this type of capacitor provide data relating relative humidity (%RH) to the capacitance of the capacitor, therefore one way of measuring %RH is to measure the capacitance of this capacitor and map this value to a corresponding %RH value provided by the manufacturer of the capacitor. One way capacitance may be measured is to include the capacitor in a circuit configuration that uses the capacitor to create an oscillating voltage signal who's frequency is dependent on the capacitor and then relate that frequency back to the capacitance value. After obtaining the capacitance value based on the frequency of the oscillating signal, the humidity value can be determined. Because the frequency of the oscillating signal is directly related to the capacitance of the capacitor and the capacitance of the capacitor is directly related to the %RH of the environment where the circuit is stored, the frequency of the oscillating signal can be directly related to the %RH of the environment. Since the frequency of the oscillating signal can be directly related to the %RH, a circuit using a comparator, a counter, and a microprocessor may be designed to provide humidity measurements. This circuit and its details are described in the following description.

A comparator can be configured to create an oscillator. This is shown in FIG. 1 where IC102 is a comparator. A reference voltage on node 100 is established by the voltage divider created by the resistors R104 and R106 in series, and the feedback resistor R102. R104 is connected to the positive supply, VCC and node 100. R106 is connected to node 100 and GND. A feedback resistor, R102 is connected to the output of the comparator, node 104, and node 100. The reference voltage, established by the circuit defined by the resistors R102, R104, and R106, should be as precise as possible in order to minimize variations in measurements of %RH from board to board. However, the precision of the resistors can be less precise in applications were variations in value are not as important or cost is more important. The values of resistors R102, R104, and R106 have a tolerance of 0.1% in this particular example. The oscillator frequency is determined by the combination of the reference voltage on node 100, and the RC delay created by the resistor R108 and the capacitor C102. R108 is connected to the output of the comparator at node 104 and to one node of the capacitor C102 at node 102. The other node of the capacitor C102 is connected to GND. The negative input of the comparator is connected to node 102 and the positive input of the comparator is connected to node 100. In this configuration, when the voltage on node 102 is higher than the reference voltage on node 100, the output of IC102, node 104 will be negative. When the output of IC102, node 104 is negative, the capacitor tied to node 102 will start to discharge through R108 into node 104. As the capacitor, C102 discharges, the voltage on node 102 will be lowered until it is below the reference voltage on node 100. When this occurs, the output of IC102, node 104 will go positive and begin charging the capacitor, C102, through R108 to a higher voltage. When the voltage on node 102 is higher than the reference voltage on node 100, the output voltage of the comparator, node 104 will transition to a low value. The continual charging and discharging of the capacitor, C102 creates an oscillator whose frequency is dependent on the RC delay time of C102 and R108, as well as the reference voltage on node 100. When the capacitance of C102 varies, the frequency of the oscillator changes. This change in frequency needs to be detected and stored. The following describes how the frequency is detected and how it is stored.

The oscillating signal from the output of the comparator, node 104 is connected to the input of a counter, IC104. The counter, IC104 sequentially counts the number of transitions from a low voltage to a high voltage for a time long enough to get an accurate count and sends that number to the microprocessor, IC106, where it is stored. The microprocessor, IC106, adds ten of these values together and stores the result. Each time the sum has been calculated, it is added to thirty-one times the previously stored sum, and divided by thirty-two and then this new value is stored. This creates a "weighted" average of the two most recent sums. This weighted average value is then used to determine the corresponding %RH found in a "look-up" table in the microprocessor. The sensitivity of the humidity dependent capacitor C102 and the sensitivity of the comparator IC104 influence the accuracy of the measurements taken. In order for the %RH measurements between different boards containing the described humidity sensing circuit to be consistent, the capacitor C102, the resistors R102, R104, R016, and R108, and the comparator IC102 should have small variance in their values. Different types of capacitors and comparators were tired with varying results. Another method that may be used is to calibrate each board containing the circuit with a reference humidity. In this case, a known relative humidity can be established and the frequency of each oscillator on each board can be measured. The microprocessor on each board would then have a different "look-up" table to translate the frequency measured to a humidity value. This method may require more initial set-up time however. The advantage of this method is that the parts used on these boards do not have to be as closely matched as in the other method.

The use of a Humirel THS1101 humidity dependent capacitor and a Philips 555 timer as a comparator and two (1%) tolerance resistors, along with a microprocessor configured in a similar circuit as FIG. 1 resulted in a 25%variance in %RH between several boards. This was not accurate enough to track tape failures due to humidity without calibration to a known %RH. The best solution used a General Eastern Instrument's GCAP-2-S-C humidity dependent capacitor, C102, and a Philips LM393 comparator, IC102 with high precision resistors (0.1%) for R102, R104, R106, and R108. The variation between boards using this combination showed only a variation of +/−6%in %RH. This degree of consistency between boards made it possible to track failures due to %RH without calibrating each board to a known %RH.

The foregoing description of the present invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. An electronic system for measuring humidity when a magnetic tape fails comprising:

a capacitor whose capacitance varies as a function of humidity;

discrete resistors;

a comparator configured with the capacitor and the resistors to create an oscillating voltage whose frequency is based on the capacitance of the capacitor;

a counter that counts the number of transitions created by the frequency of the oscillating voltage;

a microprocessor that stores data from the counter and translates said data to a relative humidity value;

wherein said microprocessor detects when said magnetic tape fails and determines the relative humidity at the time of said failure.

2. A method for correlating relative humidity measurements to magnetic tape failures comprising the following steps:

measuring the relative humidity of the environment where said magnetic tapes are stored;

storing the measured relative humidity values;

correlating relative humidity values where magnetic tape failures occur.

* * * * *